United States Patent
Kidane et al.

(10) Patent No.: US 9,393,203 B2
(45) Date of Patent: *Jul. 19, 2016

(54) OSMOTIC DRUG DELIVERY SYSTEM

(71) Applicant: Supernus Pharmaceuticals, Inc., Rockville, MD (US)

(72) Inventors: Argaw Kidane, Montgomery Village, MD (US); Padmanabh P Bhatt, Rockville, MD (US)

(73) Assignee: Supernus Pharmaceuticals, Inc., Rockville, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 14/881,374

(22) Filed: Oct. 13, 2015

(65) Prior Publication Data
US 2016/0030355 A1 Feb. 4, 2016

Related U.S. Application Data

(60) Division of application No. 14/265,630, filed on Apr. 30, 2014, now abandoned, which is a continuation of application No. 11/412,100, filed on Apr. 27, 2006, now Pat. No. 8,747,897.

(51) Int. Cl.
| | |
|---|---|
| *A61K 9/24* | (2006.01) |
| *A61K 9/20* | (2006.01) |
| *A61K 9/00* | (2006.01) |
| *A61K 9/16* | (2006.01) |
| *A61K 31/557* | (2006.01) |
| *A61K 31/5575* | (2006.01) |
| *A61K 31/5585* | (2006.01) |
| *A61K 9/28* | (2006.01) |
| *A61K 31/192* | (2006.01) |

(52) U.S. Cl.
CPC ............ *A61K 9/2013* (2013.01); *A61K 9/0004* (2013.01); *A61K 9/1623* (2013.01); *A61K 9/1652* (2013.01); *A61K 9/2077* (2013.01); *A61K 9/28* (2013.01); *A61K 31/192* (2013.01); *A61K 31/557* (2013.01); *A61K 31/5575* (2013.01); *A61K 31/5585* (2013.01)

(58) Field of Classification Search
None
See application file for complete search history.

(56) References Cited

U.S. PATENT DOCUMENTS

| | | |
|---|---|---|
| 4,434,164 A | 2/1984 | Lombardino |
| 5,466,713 A | 11/1995 | Blitstein-Willinger et al. |
| 5,506,265 A | 4/1996 | Blitstein-Willinger |
| 6,046,177 A | 4/2000 | Stella et al. |
| 6,706,283 B1 | 3/2004 | Appel et al. |
| 6,766,817 B2 | 7/2004 | da Silva |
| 6,918,404 B2 | 7/2005 | Dias da Silva |
| 7,066,586 B2 | 6/2006 | da Silva |
| 7,285,255 B2 | 10/2007 | Kadlec et al. |
| 7,384,978 B2 | 6/2008 | Phares et al. |
| 7,417,070 B2 | 8/2008 | Phares et al. |
| 7,611,728 B2 | 11/2009 | Kidane et al. |
| 8,747,897 B2 | 6/2014 | Kidane et al. |
| 9,278,901 B2 | 3/2016 | Phares et al. |
| 2001/0038855 A1 | 11/2001 | Desjardin et al. |
| 2001/0056095 A1 | 12/2001 | Mylari |
| 2005/0053653 A1 | 3/2005 | Kidane et al. |
| 2005/0165111 A1 | 7/2005 | Wade et al. |
| 2005/0208135 A1 | 9/2005 | Viswanathan et al. |
| 2005/0239719 A1 | 10/2005 | Zeldis |

FOREIGN PATENT DOCUMENTS

| | | |
|---|---|---|
| WO | WO 97/37640 A | 10/1997 |
| WO | WO 98/18452 A1 | 5/1998 |
| WO | WO 99/01121 A | 1/1999 |
| WO | WO 02/055136 A | 7/2002 |
| WO | WO 03/092660 A | 11/2003 |
| WO | WO 2005/020929 A | 3/2005 |
| WO | WO 2005/023228 A | 3/2005 |

OTHER PUBLICATIONS

McClelland et al., "The solubility-modulated osmotic pump: in vitro/in vivo release of diltiazem hydrochloride," Pharm. Res., Jan. 1991, 8(1):88-92.
Communication of a Notice of Opposition for EP 07755989 dated Aug. 21, 2012.
D4a: Product Information Treprostinil, 2012.
D4b: Product Information Treprostinil (diethanolamine salt), 2012.
Letter to Supernus Pharmaceuticals, Inc. from Louis, Pohlau and Lohrentz informing of Notice of Opposition, Sep. 11, 2012.
Sandoz AG Opposition against EP 2010189 dated Aug. 8, 2012.
Verma et al. "Formulation aspects in the development of osmotically controlled oral drug delivery system," Journal of Controlled Release, 2002, 79:7-27.
Verma et al. "Osmotic pumps in drug delivery," Critical Reviews in Therpeutic Drug Carrier Systems, 2004, 21(6):477-520.
Verma et al., "Osmotically controlled oral drug delivery," Drug Development and Industrial Pharmacy, 2000, 26(7):695-708.
Voight et al., "Lehrbuch der pharmazeutischen Technologie," 1987, with English translation.
Reisbig et al., "Staggered transtion to epoprostenol from treprostinil in pulmonary atrial hypertention," Ann. Of Pharmacotherapy, 2005, 39(4):739-743 (abstract).
McSwain et al., "Dose proportionality of treprostinil sodium adminstered by continuous subcutaneous and intravenous infusion," J. Clin. Pharmacol., Jan. 2008, 48(1):19-25.
Voswinckel et al., "Metered dose inhaler delivery of treprostinil for the treatment of pulmonary hypertenstion," Pulm. Pharmacol. Ther., Feb. 2009, 22(1):50-56 (abstract).
Gotzkowsky et al., "Lack of a Pharmacokinetic Interaction Between Oral Treprostinil and Bosentan in Healthy Adult Volunteers," Journal of Clinical Pharmacology, Jul. 2010, 50(7):829-834 (abstract).
Gomberg-Maitland et al., "Prostacyclin therapies for the treatment of pulmonary arterial hypertension," European Respiratory Journal, 2008, 31(4):891-901.

(Continued)

*Primary Examiner* — Hasan Ahmed
(74) *Attorney, Agent, or Firm* — Foley & Lardner LLP (57) ABSTRACT

An oral osmotic pharmaceutical delivery system comprises a highly water-soluble drug exhibiting an erratic or an incomplete release profile when formulated in an elementary osmotic pump delivery system and at least one release enhancing agent.

23 Claims, 7 Drawing Sheets

(56) References Cited

OTHER PUBLICATIONS

Material Safety Data Sheet of Glipizide, Oct. 9, 2005.
"Full Prescribing Information" page of Remodulin® available from United Therapeutics Corp. at www.remodulin.com, downloaded Jan. 2011.
International Search Report for PCT/US2007/009969 dated Jul. 11, 2007
Bighley et al., "Salt Forms of Drugs and Absorption," Encyclopedia of Pharmaceutical Technology, Swarbrick et al., Eds., 1995, 13:453-499.
Simonneau et al., "Continuous Subcutaneous Infusion of Treprostinil, a Prostacyclin Analogue, in Patients with Pulmonary Arterial Hypertention," Am. J. Respir. Crit. Care Med., 2002, 165:800-804.
Amendment and Reply Under 37 CFR 1.116 filed May 18, 2016, in co-pending U.S. Appl. No. 14/881,379.

OSMOTIC DRUG DELIVERY SYSTEM

CROSS-REFERENCE TO RELATED APPLICATIONS

This application is a divisional of U.S. application Ser. No. 14/265,630, filed Apr. 30, 2014, which is a continuation of U.S. application Ser. No. 11/412,100, filed Apr. 27, 2006, the entire contents of which are incorporated herein by reference.

The present invention is directed to the oral osmotic delivery of therapeutic compounds that have high aqueous solubility but demonstrate an erratic or incomplete, e.g., release from an elementary osmotic pump (EOP) delivery system. e.g., due to reduced solubility in the presence of other components of a dosage form. The limited solubility in the presence of other components of a dosage form often also results in an incomplete release. Medicinal agents that exhibit reduced solubility in the presence of other components benefit from the release-enhancing agents (also know as release promoters) in the dosage form in order to achieve complete release. The present invention is directed to oral osmotic drug delivery systems for all therapeutic agents with inherent high solubility but limited release from an osmotic dosage form.

Extended release tablets that have an osmotically active drug core surrounded by a semi-permeable membrane are known in the art. These osmotic dosage forms function by allowing water from gastric or intestinal fluid, to flow through the semi-permeable membrane and dissolve the active ingredient in the core so it can be released through one or more passageways in the membrane. An elementary osmotic pump (EOP) delivery system requires that the drug is in solution in order to be delivered in a controlled and predictable manner. The drug in solution is pumped out due to the osmotic gradient generated across the semi-permeable membrane.

Solubility of the drug in aqueous media is usually used as a reference to assess whether there is a need for a solubilizer in the core formulation. Several drug delivery platforms were developed to overcome the challenges of limited solubility of poorly soluble medicinal agents. If the drug is insoluble, an elementary osmotic pump system will not function properly. One approach for delivering pharmaceutical agents that are insoluble in aqueous solvents was developed by Kuczynski et al., (U.S. Pat. No. 5,545,413). In their approach, the interior of the tablet or capsule is characterized by two core layers, one containing the pharmaceutical agent (again to be released through openings, or holes, in the wall of the tablet or capsule) and the other being a layer of material that swells when coming into contact with water. The material that swells or expands to an equilibrium state when exposed to water or other biological fluids is referred to as an "osmopolymer". This volume expansion is used to physically force the pharmaceutical agent out through the openings, which have been formed in the wall, shell or coating during the manufacture. The pharmaceutical agent is primarily released in the form of insoluble particles, which therefore have limited bioavailability. This method has commonly been referred to as the "push/pull" approach. See, for example, U.S. Pat. Nos. 5,422,123; 4,783,337; 4,765,989; 4,612,008; and 4,327,725. The patent literature has taught this approach for delivering adequate doses, at controlled rates and for extended times, of a broad variety of drugs.

Other osmotic delivery systems have also been described. See, for example, U.S. Pat. Nos. 4,609,374; 4,036,228; 4,992,278; 4,160,020; and 4,615,698. The osmopolymers used in these types of systems are components whose function is to swell when they interact with water and aqueous fluids. This swelling effect is defined in these patents as a property of imbibing fluid so as to expand to a very high degree, usually exhibiting a 2-to 50-fold volume increase.

Rudnic et al., (U.S. Pat. Nos. 6,110,498; 6,284,276; 6,361,796, and 6,514,532) used sodium lauryl sulfate and other solubilizers to enhance the solubility of glipizide, a poorly soluble drug, to deliver it from an elementary type of osmotic system in a sustained manner. This system of Rudnic is comprised of (a) a semi-permeable wall that maintains its integrity during pharmaceutical delivery, and which has at least one passage there through; (b) a single, homogeneous composition within said wall, which composition consists essentially of (i) a pharmaceutically active agent, (ii) at least one non-swelling solubilizing agent which enhances the solubility of the pharmaceutically active agent; (iii) at least one non-swelling osmotic agent, and, optionally, (iv) a non-swelling wicking agent dispersed throughout the composition which enhances the surface area contact of the pharmaceutical agent with the incoming aqueous fluid.

Thombre et al., (U.S. Pat. No. 5,697,922) used meglumine as a solubilizing agent for glipizide. This patent suggests coating meglumine with semi-permeable polymeric films to extend the release of the solubilizer from the core. Thombre et al argued that non-encapsulated solubilizers would leave the core early, leaving the drug behind in an unsolubilized form. This loss of solubilizer results in an erratic release or no release at all. The problem with this approach is that it is very complex, because it involves coating of the solubilizing excipient during the manufacture of the tablet. This process limits its practical significance. Also, the amount of solubilizing excipient used in this approach is exceedingly high. See also, U.S. Pat. No. 5,698,220, which discloses the use of 90% meglumine (aka, N-methylglucamine) in an osmotic dosage form for delivering glipizide.

This prior art does not address drugs that are highly water soluble when tested alone but manifest limited solubility and an erratic or incomplete release in the presence of other components of an osmotic dosage form.

The present invention overcomes the inadequacies of the prior art in the delivery of medicinal agents that are highly soluble in water but have challenges in release from osmotic dosage forms. While there are several approaches to deal with the delivery of poorly soluble drugs in osmotic delivery systems, none of these approaches deal with the problem of an incomplete and erratic release of medicinal agents which are highly water soluble but of limited solubility and release in the presence of other components of a dosage form. Such drugs may be exemplified by prostacyclins that are valuable pharmacologically active compounds used in the treatment of/for: pulmonary hypertension, pulmonary arterial hypertension (PAH), peripheral vascular disease (PVD), ischemic diseases (e.g. peripheral vascular disease, Raynaud's phenomenon, Scleroderma, myocardial ischemia, ischemic stroke; renal insufficiency), heart failure (including congestive heart failure), conditions requiring anticoagulation (e.g. post MI, post cardiac surgery), thrombotic microangiopathy, extracorporeal circulation, central retinal vein occlusion, atherosclerosis, inflammatory diseases (e.g. psoriasis), hypertension, cancer or other conditions of unregulated cell growth, cell/tissue preservation and other emerging therapeutic areas where prostacyclin treatment appears to have a beneficial role.

Prostacyclins are characterized by a very short half-life ranging from several minutes to several hours, which makes sustained oral delivery of this compounds problematic. A chemically stable analog of prostacyclin, treprostinil, has presented problems in sustained oral delivery with the prior art. Although treprostinil sodium (Remodulin®) is approved by the Food and Drug Administration (FDA) for subcutaneous and intravenous administration, treprostinil as the free acid has an absolute oral bioavailability of less than 10%. Though oral preparations of treprostinil have been disclosed (e.g. US Patent applications 20050165111 and 20050282903, and U.S. Pat. Nos. 5,153,222, 5,028,628, and 6,054,486), none of these publications addresses an issue of an erratic/incomplete release of treprostinil from oral controlled release dosage forms. US patent publication 20050282901-to Phares discloses a composition comprising a prostacyclin (treprosinil) and an additional cardiovascular agent that enhances the oral bioavailability of treprostinil. However, no teaching has been suggested for osmotic sustained release, high bioavailability preparations having treprostinil as the only active agent.

SUMMARY OF THE INVENTION

Accordingly, there is clinical interest in a safe and effective method for full and sustained delivery of treprostinil or its salts or derivatives via oral administration. This invention pertains to an osmotic drug delivery system that incorporates release-promoting agent(s) (release enhancers) to achieve complete and predictable release of such medicinal agents. It additionally pertains to the methods for oral delivery of prostacyclins, treprostinil in particular, in sustained release solid dosage forms.

The present invention provides for complete and predictable release of highly water-soluble medicinal agents (thus not ignoring a solubility enhancer(s)) with water solubility of at least 30 mg/ml or higher, whose release from an osmotic controlled/sustained release dosage form, i.e., a standard osmotic delivery system, is erratic and/or incomplete. For the purposes of this invention, an erratic release is defined as an inconsistent release among tablets of similar composition (mean (n=6) percent released differing by more than 25%), and an incomplete release is defined as less than complete release (80% or less) in 10-12 Hrs for a drug given twice a day; 80% or less in 16-24 Hrs for a drug that is given once a day.

These erratic and/or incomplete releases refer to in vitro release, measured conventionally, e.g., by USP dissolution method described in the Figures.

By a "standard osmotic delivery system" herein is meant an elementary osmotic pump (EOP) system. An EOP is very well known to those skilled in the art. This system can be used to test for drugs which are "erratic" or give an incomplete release profile, as defined. See, e.g., Felix Theeuwes, Elementary Osmotic Pump, Journal of Pharmaceutical Sciences, Vol. 64, No. 12, Pp 1987-1991, December 1975.

The release enhancing agents (also called release promoters) used in this invention promote the release of the medicinal agents while delivering the drug in a controlled and pre-determined rate. The present invention also provides for controlled and sustained release of a class of medicinal agents, such as the prostacyclins, which exhibit a very short half-life ranging from several minutes up to three hours, exemplified here by treprostinil or its salts or derivatives.

The invention pertains to the oral delivery of such agents in a controlled and predictable manner to meet specific therapeutic goals. Preferably, the invention relates to drugs and systems wherein in vivo release profiles ($C_{MAX}$ and/or AUC and/or $T_{MAX}$) can be accurately predicted from standard in vitro dissolution profiles, e.g, with sufficient reliability to routinely achieve desired in vivo profiles.

Other objects, features, and advantages of the present invention will become apparent from the following detailed description. It should be understood, however, that the detailed description and the specific examples, while Indicating preferred embodiments of the present invention, are given by way of illustration only, since various changes and modifications within the spirit and scope of the invention will become apparent to those skilled in the art from the detailed description.

BRIEF DESCRIPTION OF DRAWINGS

Various features and attendant advantages of the present invention will be more fully appreciated as the same becomes better understood when considered in conjunction with the accompanying drawings, in which like reference characters designate the same or similar parts throughout the several views, and wherein.

The present invention provides an alternative to solving the problem of the controlled release, osmotic delivery of pharmaceutical agents that have high aqueous solubility (at least 30 mg/ml), and preferably, do not need or benefit from solubility enhancers as in the prior art, but rather unpredictable solubility in the presence of other core excipients. Unpredictable and erratic solubility in the core formulation results in the unpredictable and rather low extent of drug release. Such erratic solubility in the core also exacerbates the effects of external environmental variables such as pH, agitation, and ionic strength on the rate and extent of drug release from the dosage form. These solubility and delivery difficulties are overcome by incorporation into an osmotic delivery system of the present invention of release enhancing agents selected to enhance the solubility of the drug in the core irrespective of the core environment and to enable the complete release of such drugs from an osmotic system. Thus, an osmotic delivery system of the present invention comprises: a) at least one medicinal agent with high aqueous solubility that exhibits limited and/or erratic and unpredictable release when formulated into an osmotic dosage from; (b) at least one release enhancing agent; (c) at least one osmotic agent; (d) optionally, a binder to aid tableting; (e) optionally, at least one lubricant to aid the tableting process; (f) typically at least one coating polymer; (g) optionally, at least one plasticizer.

For the purpose of this application, the following definitions of terms are given:

The terms "complexing agents" and "micelle forming agents" are used herein as described in Chapters 14 and 20, respectively, of the 20$^{th}$ edition of Remington's The Science and Practice of Pharmacy (20$^{th}$ ed., Lippincott, Williams and Williams, 2000).

A wicking agent is defined as any material with the ability to draw water into the network of a delivery dosage form. By so doing, a wicking agent provides enhanced flow channels for the pharmaceutical agent which has been made predominantly into its solubilized form.

Suitable release enhancing agents include wicking agents, such as high HLB surfactants (for example Tween 20, Tween 60 or Tween 80; ethylene oxide propylene oxide block copolymers (aka Pluronics®),), ionic surfactants such as sodium lauryl sulfate, sodium docusate, non-swelling hydrophilic polymers such as cellulose ethers, and polyethylene glycols (PEGs); complexing agents such as: polyvinyl pyrrolidone, cyclodextrins and non-ionic surface active agents; and micelle forming agents, which may be surface active agents such as Tweens-(Poly(ethylene Oxide) modified sorbitan monoesters), Spans (fatty acid sorbitan esters), sodium lauryl sulfate, and sodium docusate.

The release enhancing agents are incorporated in the core tablet formula and constitute from 0.5% to 90% by weight of the formula, preferably from 1% to 50%. Most preferably, release-enhancing agents constitute from 1% to 20% by weight of the formulation. They can be incorporated during granulation or post-granulation. The release enhancing agent(s) can be added in the form of solid powder or can be dissolved in the granulating liquid and sprayed during granulation. In order to achieve intimate mixing with the drug(s) the release enhancing agent can be mixed with the drug alone before the other excipients are incorporated. Alternatively, the release enhancing agent(s) and the drug can be dissolved in the granulating liquid and sprayed during granulation. In yet another way, the release enhancing agent(s) and the drug can be dissolved in a solvent, and when the solution is dried, the solid mass thus obtained can be milled and then mixed with the rest of the excipients for further processing.

Osmotic agents are well known to those skilled in the art. Osmotic agents suitable for the present invention are simple sugars such as sucrose, xylitol, glucose, lactose; salts such as sodium chloride, potassium chloride; low molecular weight hydrophilic polymers such as cellulose ethers, maltodextrins, and cyclodextrins. Osmotic agents can be incorporated in the formulation of this invention in the amount of from 1% by weight to 90% by weight, preferably from 5% to 80% and most preferably from 10% to 80% by weight. Osmotic agents are typically incorporated in the formula during granulation.

The granules can also be blended with other excipients as needed to aid the manufacturing of the desired dosage form: tablets, capsules or pellets. Tablets are compressed on a standard rotary tablet press.

The core tablet is typically coated with a semi-permeable membrane containing at least one plasticizer. The coating polymer is dissolved with at least one plasticizer in an appropriate solvent or a mixture of solvents and sprayed on the tablets for coating. The coating polymers include, but are not limited, to cellulose acetate. The coating membrane preferably also contains at least one plasticizer to improve flexibility and durability of the coat. Such plasticizers include, but are not limited to, triethyl citrate (TEC), propylene glycol (PG), or mixtures thereof in ratios of TEC to PG ranging from 25:75 to 75:25; Tween 80, polyethylene glycols (PEGs); other polyoxyethylene sorbitan esters, triacetin, diethyl phthalate, mineral oil, tributyl sebacate, and glycerol. The coating level can vary from 1% to 25%, preferably from 2% to 20%, and most preferably from 3% to 10% by weight.

The semi-permeable wall also includes at least one opening to provide for the osmotic delivery of the drug(s). In general the at least one opening has a diameter of from 50 μm to 1000 μm, preferably from 100 μm to 800 μm. The opening is formed by drilling using a laser or any other appropriate hole drilling system. The opening can be of any shape. The various shapes contemplated for this invention include, but are not limited to round, cross-shaped, rectangular, diamond, star, and square shapes. As the dosage unit (osmotic tablet) imbibes water, the release-enhancing agents go into solution providing an environment for the drug to dissolve. The osmotic agent(s) in the core tablet draws water into the core tablet creating an osmotic gradient across the semi-permeable membrane. The osmotic gradient pushes the drug in the solution out through the laser-drilled hole.

This invention is not limited to a particular dosage form such as tablets. The dosage form containing the appropriate release-enhancing agents can be prepared, e.g., in the form of capsules or pellets. Once the capsule is filled with the appropriate combination of drugs, release-enhancing agents and excipients, it is coated with a semi-permeable membrane. At least one opening is drilled through the semi-permeable membrane to allow drug release.

The oral osmotic delivery system of the present invention provides for a complete and predictable release of drugs with high water solubility but with an incomplete or erratic release from a standard osmotic formulation. This complete and predictable release is achieved by incorporation of at least one release-enhancing agent into the formulation. The release of such drugs from the formulation of the invention is unaffected by the core environmental variables such as pH and ionic strength. Such release is also independent on the extent of agitation. Therefore, the dosage form of the invention is robust and provides predictable release of the medicinal agent. The dosage form also provides in vivo release profiles that can be predicted based on in vitro release profiles. The dosage form in accordance with this invention additionally provides for a controlled release of a medicinal agent that allows for a twice to once daily administration to achieve therapeutic value. Such administration improves patient compliance. The controlled delivery of the medicinal agent will result in an essentially flat pharmacokinetic profile that reduces side effects associated with spikes in blood concentration of the medicinal agent.

The present invention is exemplified by treprostinil, a drug with particularly poor oral delivery and a short half-life, which has presented problems with the prior art technology. Treprostinil is a chemically stable analog of prostacyclin and is approved by the Food and Drug Administration (FDA) for subcutaneous and intravenous administration using a specialized pump to deliver the drug over an extended period of time. This pump allows for the delivery of the drug to the patient at a controlled rate. The drawbacks to this mode of administration are that it is complex, expensive and results in a reaction at the site of the injection. The present invention provides for an oral delivery of this drug at a controlled rate that results in a flat pharmacokinetic profile. The advantages of a controlled sustained release oral administration over injection are valuable to those skilled in the art. Particularly, the present invention provides an orally administered sustained release formulation of Treprostinil effective to produce plasma concentrations varying between a Cmin of 0.1 to 0.2 ng/ml to a maximum plasma concentration of treprostinil of about 0.5 ng/ml to about 2 ng/ml for a time of about 2 hours to 8 hours.

The formulation may be designed to provide desired steady-state blood levels of the drug in a twice-a-day regimen. Still further, the formulation may be adjusted to once-daily dosing of treprostinil in an extended release preparation that also provides a desired therapeutically effective plasma drug concentration profile.

The present invention also provides a method of using prostacyclins, and especially treprostinil, therapeutically of/for: pulmonary hypertension, pulmonary arterial hypertension (PAH), ischemic diseases, heart failure, conditions requiring anticoagulation, thrombotic microangiopathy, extracorporeal circulation, central retinal vein occlusion, atherosclerosis, peripheral vascular disease, Inflammatory diseases, hypertension, cancer or other conditions of unregulated cell growth, cell/tissue preservation and other emerging therapeutic areas where prostacyclin treatment appears to have a beneficial role. A preferred embodiment of the invention is a method of treating pulmonary arterial hypertension and/or peripheral vascular disease in a subject comprising orally administering a pharmaceutically effective amount of a prostacyclin analogue in a sustained-release osmotic dosage formulation. In addition to prostacyclins, other therapeutic agents will benefit from this invention. They may be represented by such highly water soluble pharmaceutical agents as antidepressants, for example citalopram HCl, fluoxetine HCl, and protriptyline; antipsychotic agents, such as molindone HCl and chlorpromazine HCl; anxiolytic agents such as trifluperazine HCl and clorazepate dipotassium; antibiotics such as bleomycin sulfate and clindamycin HCl; antihypertensive agents such as atenolol, lisinopril, metoprolol succinate, bisoprolol fumarate, hydrochlorothiazide, quinapril HCl, propranolol HCl, perindopril erbumine, enalapril maleate, and captopril, among others; antineoplastic agents such as terazosin HCl and tamoxifen citrate; drugs used to treat Parkinson's disease, for example biperidine HCl; antiepileptic drugs, such as gabapentin and tiagabine HCl, anticholinergic drugs, such as glycopyrrolate and, trospium chloride; antiallergics such as promethazine HCl; antiangina drugs such as isosorbide dinitrate and nadolol; drugs for treatment of an orthostatic hypotension such as midodrine HCl; attention deficit hyperactivity disorder (ADHD) drugs such as amphetamines; pain management medications such as hydromorphone HCl, codeine phosphate and meperidine HCl, and any other highly water soluble drugs not mentioned above whose complete release from a standard osmotic dosage form is not achieved. Unless otherwise specified, "a" or "an" means "one or more". As will also be understood by one skilled in the art, all language such as "up to," "at least," "greater than," "less than," "more than" and the like include the number recited and refers to ranges which can be subsequently broken down into subranges as discussed above. In the same manner, all ratios disclosed herein also include all subratios falling within the broader ratio. Furthermore, one skilled in the art will also readily recognize that where members are grouped together in a common manner, such as in a Markush group, the present invention encompasses not only the entire group listed as a whole, but each member of the group individually and all possible subgroups of the main group. Other objects, features, and advantages of the present invention will become apparent from the following examples. It should be understood, however, that the detailed description and the specific examples, while indicating preferred embodiments of the present invention, are given by way of illustration only, since various changes and modifications within the spirit and scope of the invention will become apparent to those skilled in the art from the detailed description.

EXAMPLES

In order that this invention may be better understood, the following examples are set forth. These examples are for the purpose of illustration only and are not to be construed as limiting the scope of the invention in any manner. Numerous other variations of the present invention will be appreciated by those skilled in the art, in view of the disclosure herein. The exact compositions, methods of preparation and embodiments shown are not limiting of the invention, and any obvious modifications will be apparent to one skilled in the art.

Example 1

Granulation of Treprostinil Osmotic Formulation Containing Sodium Lauryl Sulfate and Megalumine as Release Enhancing Agents Table 1 provides composition of the Treprostinil osmotic tablet cores made with and without release enhancing agent:

TABLE 1

| Composition of Treprostinil osmotic granulation | | |
|---|---|---|
| Ingredients | No Release | With release enhancers |
| Treprostinil diethanolamine | 0.635% | 0.65% |
| Xylitol | 41.0% | 41.00% |
| Maltrin M150 (wet) | 1.60% | 1.40% |
| Maltrin M150 (dry) | 53.0% | 48.20% |
| Sodium Phosphate | 3% | — |
| Sodium Lauryl Sulfate | — | 5.00% |
| Meglumine | — | 3.00% |

All ingredients were screened through an 18-mesh sieve prior to granulation. Granules were manufactured by top spray granulation in Glatt's fluid bed granulator (GPCG-1 or GPCG-15 (Glatte Air Techniques Inc., Ramsey, N.J.). Two spray solutions were prepared. One solution contained Maltrin M150 (used as a binder), and the drug, treprostinil. The second solution contained Maltrin M150 only. Prescreened ingredients were charged in to the fluid bed granulator. Spray solution 1 was sprayed first followed by spray solution 2. The granulation process parameters are given in Table 2. Once all the spray solutions have been sprayed, the granules were dried in the fluid bed while monitoring the moisture level. A moisture level of less than 3% was considered acceptable. Dried granules were screened through an 18-mesh sieve.

TABLE 2

| Granulation processing parameters | | |
|---|---|---|
| | 2 Kg scale | 10 Kg scale |
| Fluid bed Granulator | GPCG-1 | GPCG-15 |
| Typical batch size (kg) | 2 | 10 |
| Inlet air temperature (° C.) | 58-63 | 58-63 |
| Exhaust air temperature (° C.) | 28-31 | 28-31 |
| Product temperature (° C.) | 31-33 | 31-33 |
| Air volume (m/s for GPCG1 and CFM for GPCG-15) | 4 | 400-500 |
| Spray rate (gm/min) | 8-9 | 120-150 |

Example 2

Tableting of Granules from Example 1

Screened granules from Example 1 were blended with magnesium stearate in a V-blender for 3-5 minutes. The blend was tableted on a Rotary tablet press using a 5/16"-round standard concave tooling (punches and dies). Tablet weight, hardness, and thickness were monitored throughout the compression run. Tablets were also analyzed for an assay and content uniformity.

Table 3 provides the composition of treprostinil core tablets:

TABLE 3

Composition of Treprostinil osmotic tablets

| Ingredients | No Release enhancer | Release enhancer(s) |
|---|---|---|
| Treprostinil diethanolamine | 0.635% | 0.65% |
| Xylitol | 41.0% | 41.00% |
| Maltrin M150 (wet) | 1.60% | 1.40% |
| Maltrin M150 (dry) | 53.0% | 48.20% |
| Na Phosphate | 3% | — |
| Sodium Lauryl Sulfate | — | 5.00% |
| Magnesium stearate | 0.75% | 0.75% |

Example 3

Coating of Tablets from Example 2

Core tablets from Example 1 were coated with a coating system containing cellulose acetate as a polymer and Poly (ethylene glycol) 3350 (PEG3350) as a plasticizer. Coating was performed in LDCS-III pan coater (Vector Corporation, Marion, Iowa). The coating solution was sprayed on the tablets in a rotating perforated pan until the desired coating level was achieved.

Example 4

Drilling Coated Tablets from Example 3 Using Laser Tablet Drilling System

A hole was drilled on the coating of the tablets from Example 3 using Lumonics laser tablet drilling system (Resonetics Inc, Nashua, N.H.). The laser power and beam diameter is adjusted to achieve desired hole size. Drilled tablets were evaluated for assay, content uniformity and dissolution.

Figure 1:
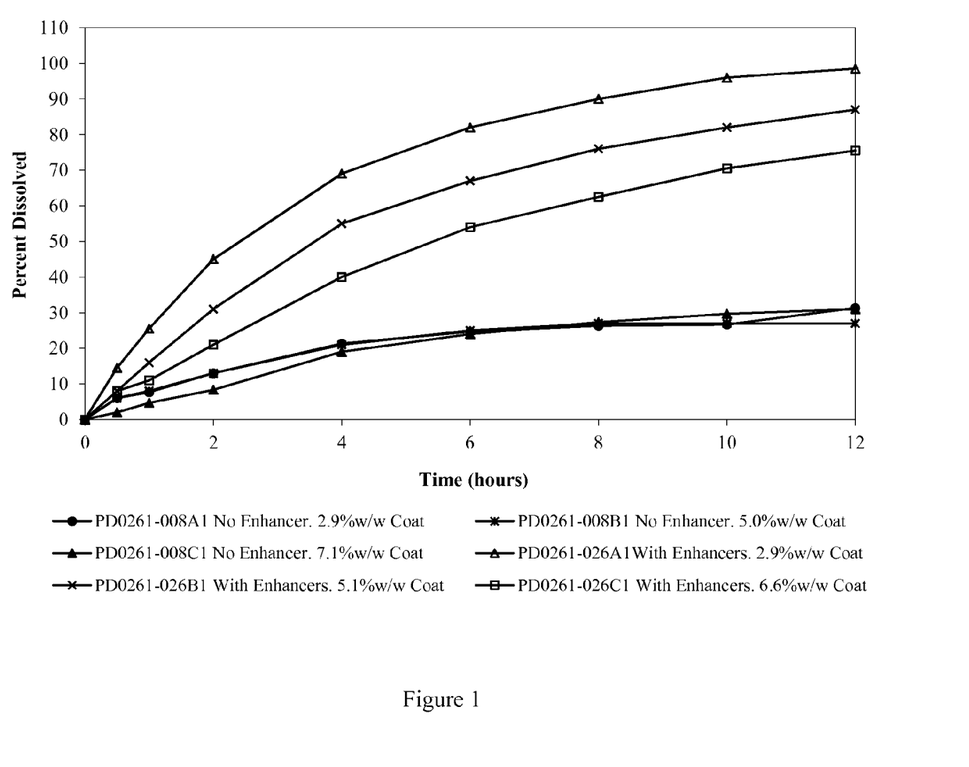
FIG. 1 depicts the dissolution profiles of Treprostinil Diethanolamine osmotic tablets with and without release enhancing agents using a USP Apparatus II at 50 RPM, Dissolution medium: of phosphate bugger (pH 6.8).

FIG. 1 shows the dissolution profiles for tablets from Example 5. Dissolution was conducted using USP Apparatus II at a paddle speed of 50 RPM. The dissolution medium was 50 mM phosphate buffer at pH 6.8. The release of treprostinil from the osmotic tablets containing release enhancer(s) can be described by a $T_{10}$ (time to release 10%) of 0.25 Hr-1 Hr; $T_{50}$ (time to release 50%) of 2 Hrs-5 Hrs, and $T_{80}$ (time to release 80%) of 6 Hrs-12 Hrs.

Example 5

Granulation and Tableting of Formulations Containing Sodium Lauryl Sulfate (SLS) as a Release Enhancing Agent

TABLE 4

Composition of SLI539 CTM granules, uncoated and coated tablets

| Formulation | Granules | Uncoated Tablets | Coated Tablets |
|---|---|---|---|
| Treprostinil diethanolamine | 0.65% | 0.65% | 0.63% |
| Xylitol CM90 | 43.32% | 43.00% | 41.71% |
| Maltrin M150 (wet) | 1.41% | 1.40% | 1.36% |
| Maltrin M150 (dry) | 49.57% | 49.20% | 47.72% |
| Sodium Lauryl Sulfate | 5.04% | 5.00% | 4.85% |
| Magnesium Stearate | N/A | 0.75% | 0.73% |
| Cellulose Acetate | N/A | N/A | 2.40% |
| Triethyl Citrate | N/A | N/A | 0.60% |
| Total | 100% | 100% | 100% |

Table 4 provides the granules and tablet composition. Granules were-manufactured by top spray granulation in a fluid bed granulator (GPCG-1 for 2 kg scale and GPCG-15 for the 10 kg scale batches). Two spray solutions were prepared. One solution contained Maltrin M150 (used as a binder), and Treprostinil diethanolamine. The second solution contained Maltrin M150 only. All ingredients were screened through an 18-mesh sieve. Sieved ingredients were charged in to the fluid bed granulator. Spray solution 1 was sprayed first followed by spray solution 2. Granulation process parameters are provided in Table 2. Once all the spray solutions have been sprayed, the granules were dried in the fluid bed granulator while monitoring the moisture level. A moisture level of less than 3% was considered acceptable. Dried granules were screened through an 18-mesh sieve. Dry granules were blended with magnesium stearate in a PK V-blender fitted with an appropriate size shell. The blend time was 3-5 minutes. The blend was then compressed on a rotary tablet press using a standard 5/16" concave tooling. Tablet weight, hardness and thickness were monitored throughout the compression run.

Example 6

Coating and Drilling of Tablets from Example 5

TABLE 5

Coating solution composition (% by weight)

| Ingredients | TEC/CA |
|---|---|
| Cellulose acetate | 5 |
| Triethyl citrate (TEC) | 1.25 |
| Acetone | 93.75 |
| Total | 100 |

Table 6 provides the tablet coating process parameters.

TABLE 6

Pan coating process parameters

| | TEC/CA |
|---|---|
| Coating System | |
| Pan Coater | O'Hara Pan Coater |
| Typical batch size (kg) | 3.5-4.0 |
| Inlet air temperature (° C.) | 38 |
| Exhaust air temperature (° C.) | 26-31 |
| Air Flow (CFM) | 110 |
| Spray air (PSI) | 23 |
| Pattern Air (PSI) | 23 |
| Pan rotation (RPM) | 12 |
| Spray rate (gm/min) | 30-50 |

TABLE 6-continued

Pan coating process parameters

| | TEC/CA |
|---|---|
| Curing | |
| Inlet air temperature (° C.) | 38 |
| Exhaust air temperature (° C.) | 26-31 |
| Air Flow (CFM) | 110 |
| Spray air (PSI) | N/A |
| Pattern Air (PSI) | N/A |
| Pan rotation (RPM) | 10 |
| Spray rate (gm/min) | N/A |
| Cool down | |
| Inlet air temperature (° C.) | Heat Off |
| Exhaust air temperature (° C.) | N/A |
| Air Flow (CFM) | 110 |
| Spray air (PSI) | N/A |
| Pattern Air (PSI) | N/A |
| Pan rotation (RPM) | 10 |
| Spray rate (gm/min) | N/A |

Tablets were charged in to the pan coater and jogged to warm-up. Coating solution was sprayed while monitoring the exhaust temperature. Tablets were coated to various coating levels by weight. Table 6 provides the coating process parameters used. Coated tablets were drilled as in Example 2, and the drilled tablets were tested for dissolution. The dissolution profiles of tablets made in this example are given in FIGS. 2-5.

Figure 2:
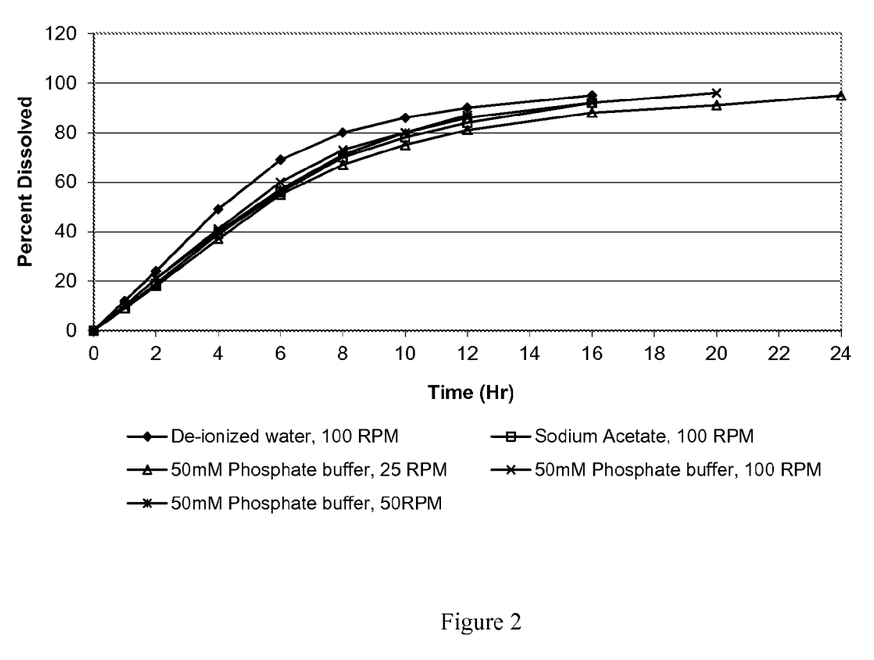
FIG. 2 shows the effect of dissolution of Treprositinil Diethanolamine Osmotic Tablets under various dissolution conditions (dissolution media, paddle speed) using USP Apparatus II.
Figure 3:
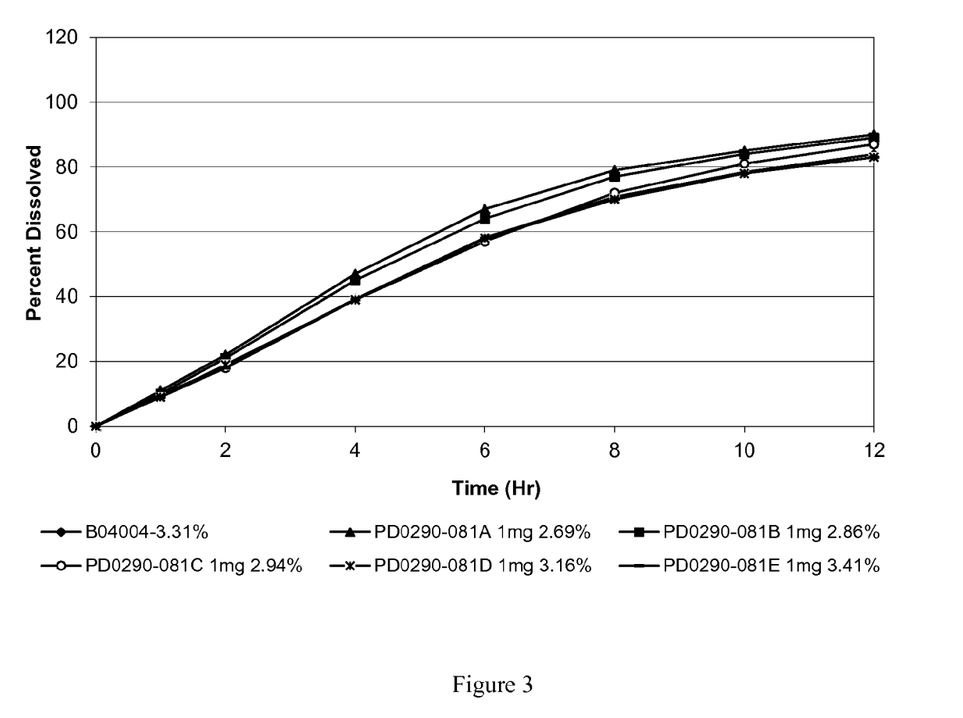
FIG. 3 shows the effect of coating levels (by weight) on the release of treprostinil from Treprostinil Diethanolamine osmotic tablets.
Figure 4:
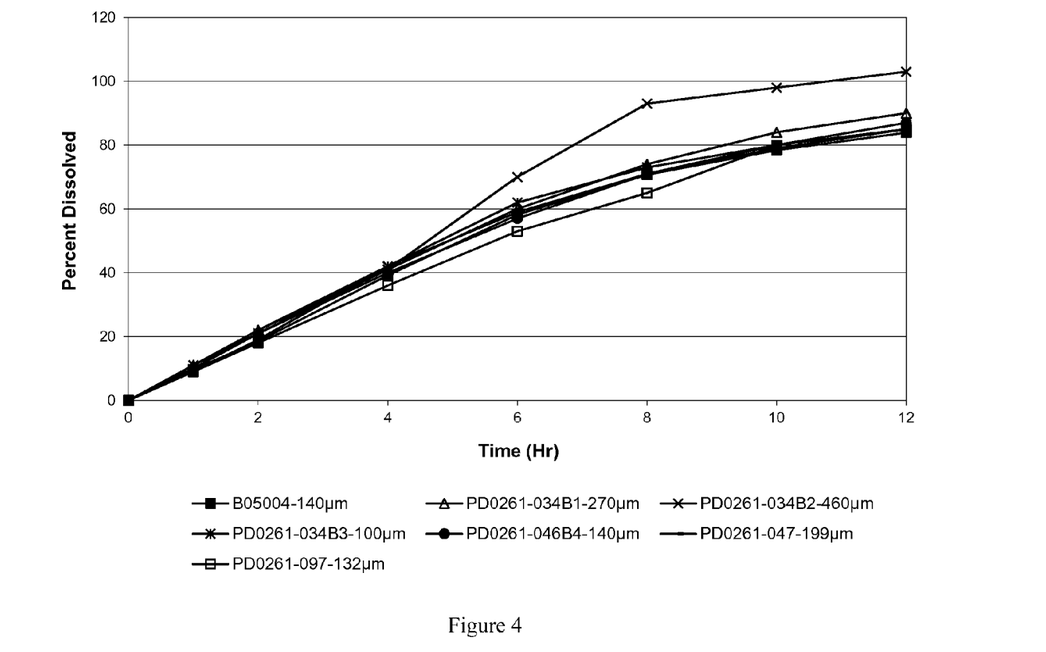
FIG. 4 shows dissolution profiles of Treprostinil Diethanolamine osmotic tablets coated to 3% weight gain and drilled to various hole sizes.
Figure 5:
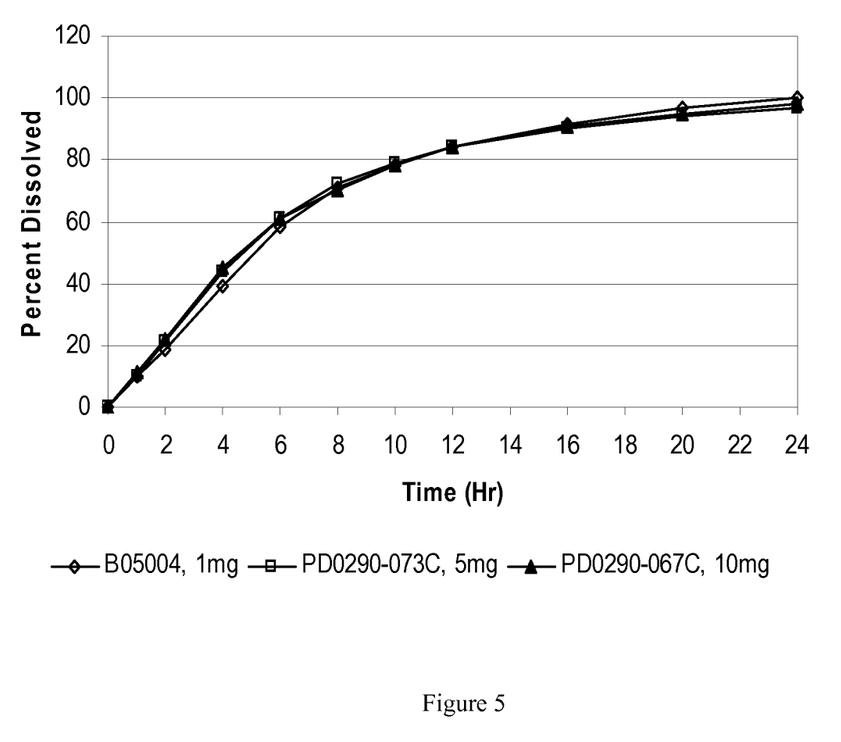
FIG. 5 shows the dissolution profiles of Treprostinil Diethanolamine osmotic tablets containing varying amounts of the active drug (1 mg, 5 mg, and 10 mg).
Figure 6:
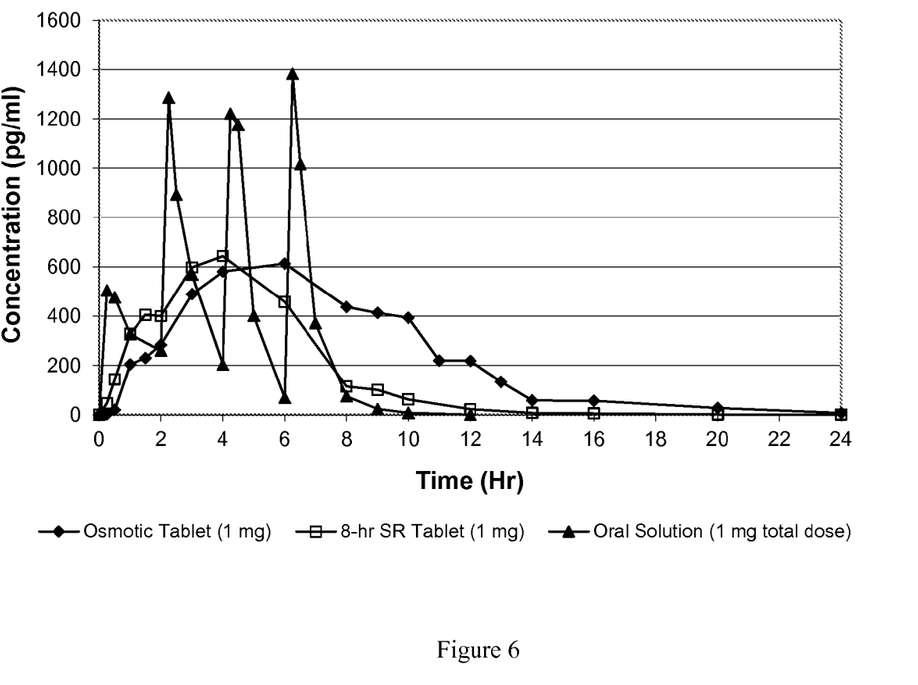
FIG. 6 shows the pharmacokinetic profiles in humans of Treprostinil Diethanolamine osmotic tablet and a reference tablet formulation versus an oral solution.

The dissolution profiles obtained can be described by $T_{10}$ (time to release 10%) of 0.25 Hr-1 Hr; $T_{50}$ (time to release 50%) of 2 Hrs-5 Hrs, and $T_{80}$ (time to release 80%) of 6 Hrs-12 Hrs. FIG. 2 shows the effect of dissolution conditions (paddle speed, ionic strength of the dissolution medium, pH of the dissolution medium) on the release of treprostinil from osmotic treprostinil tablets. FIG. 3 shows the effect of coating levels (by weight) on the release of treprostinil from osmotic treprostinil tablets. FIG. 4 shows the effect of an opening diameter on the release of treprostinil. Shown in FIG. 5 are the dissolution profiles of osmotic treprostinil tablets containing varying amounts of the active drug.

Example 7

Human Pharmacokinetic Study of Treprostinil Osmotic Tablets from Example 6

Figure 7:
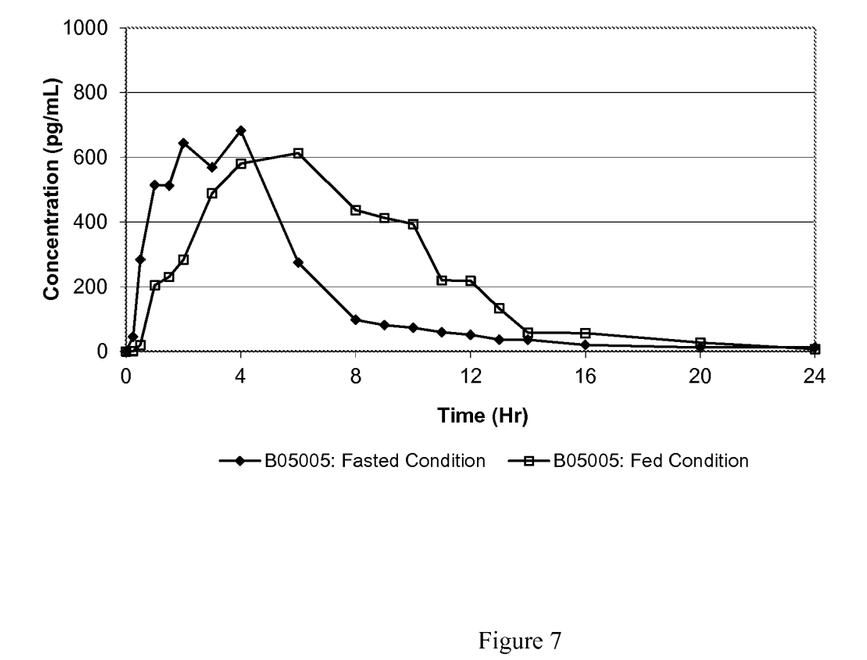
FIG. 7 shows the pharmacokinetic profiles of Treprostinil Diethanolamine 1 mg osmotic tablet when given with and without food.

The objective was to compare the safety and PK profile of the 12 Hr Treprostinil Osmotic tablet formulation (lot #B05005) with an 8 Hr Sustained Release (SR) tablet formulation in healthy volunteers. Subjects (n=10) received a single dose (1 mg) of the osmotic formulation in either fasted state or fed state (standard FDA meal). Subjects then had a washout period of 7 days and then returned to the clinic to receive the crossover treatment. On the dosing days, PK samples were collected out to 24 Hr post dose and safety was assessed until discharge from the clinic. PK samples were analyzed by a validated LC/MS/MS assay. The pharmacokinetic profiles are given in FIG. 7. Results show that the Osmotic tablet formulation provides an extended systemic exposure compared to the 8 Hr SR (sustained release) tablet formulation.

Example 8

Effect of Food on the Pharmacokinetics of Treprostinil from an Osmotic Treoprostinil Tablet The objective was to compare the safety and PK profile of the 12 Hr Treprostinil Osmotic tablet formulation (lot #B05005) in the fed and fasted state in healthy volunteers. Subjects (n=10) received a single dose (1 mg) of the osmotic formulation in either the fasted state or fed state (standard FDA meal). Subjects then had a washout period of 7 days and then returned to the clinic to receive the crossover treatment. On dosing days, PK samples were collected out to 24 Hr post dose and safety was assessed until discharge from the clinic. PK samples were analyzed by a validated LC/MS/MS assay. The pharmacokinetic profiles are given in FIG. 7. Results showed there was a difference in the PK profiles between the fed and fasted states with the fed state exhibiting longer duration of treprostinil systemic exposure. Safety parameters were similar between the fed and fasted states with very good overall tolerability.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications cited herein are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A solid dosage form comprising an oral osmotic pharmaceutical delivery composition comprising an osmotically active drug core surrounded by a semi-permeable membrane, wherein the osmotically active drug core comprises
   A) at least one solid release enhancing agent, which is a surfactant selected from the group consisting of polysorbate 20, polysorbate 60, polysorbate 80, sodium lauryl sulfate, and sodium docusate,
   and
   B) a pharmaceutically acceptable salt of treprostinil having a water solubility of at least about 30 mg/mL, and
   wherein the semi-permeable membrane allows for the osmotic delivery of the treprostinil from the osmotically active drug core.

2. The solid dosage form of claim 1, wherein the at least one solid release enhancing agent comprises sodium lauryl sulfate.

3. The solid dosage form of claim 1, further comprising at least one osmotic agent.

4. A method of treating pulmonary hypertension comprising administering orally to a human subject in need thereof a solid dosage form of claim 1.

5. The method of claim 4, wherein the pharmaceutically acceptable salt of treprostinil is treprostinil diethanolamine.

6. The solid dosage form of claim 1, wherein the composition is configured to provide a therapeutically effective plasma concentration of treprostinil in a human subject for a time from about 2 hours to about 8 hours after being administered orally to the human subject.

7. The solid dosage form of claim 1, wherein the at least one solid release enhancing agent comprises at least one of sodium lauryl sulfate and sodium docusate.

8. The solid dosage form of claim 1, wherein the pharmaceutically acceptable salt of treprostinil is treprostinil diethanolamine.

9. The method of claim 4, wherein the administering results in a therapeutically effective plasma concentration of treprostinil in the human subject for a time from about 2 hours to about 8 hours after said administering.

10. The method of claim 9, wherein a minimum value of the effective plasma concentration of treprostinil is from 0.1 ng/ml to 0.2 ng/ml.

11. The method of claim 9, wherein a maximum value of the effective plasma concentration of treprostinil in the subject is from 0.5 ng/ml to 2 ng/ml.

12. The method of claim 9, wherein said administering is performed twice a day or once a day.

13. The method of claim 9, wherein said administering is performed twice a day.

14. A solid dosage form comprising an oral osmotic pharmaceutical composition comprising (a) a therapeutically effective amount of a pharmaceutically acceptable salt of treprostinil having an aqueous solubility of at least 30 mg/ml and (b) at least one solid release enhancing agent, wherein the at least one solid release enhancing agent is a surfactant selected from the group consisting of polysorbate 20, polysorbate 60, polysorbate 80, sodium lauryl sulfate, and sodium docusate, and wherein the composition is configured to provide an effective plasma concentration of treprostinil in a human subject for a time from about 2 hours to about 8 hours after being administered orally to the human subject.

15. The solid dosage form of claim 14, wherein the at least one solid release enhancing agent comprises at least one of sodium lauryl sulfate and sodium docusate.

16. The solid dosage form of claim 14, wherein the at least one solid release enhancing agent comprises sodium lauryl sulfate.

17. The solid dosage form of claim 1, wherein the pharmaceutically acceptable salt of treprostinil is treprostinil diethanolamine.

18. A method of treating pulmonary hypertension comprising administering orally to a human subject in need thereof a solid dosage form of claim 14.

19. The method of claim 18, wherein the pharmaceutically salt of treprostinil is treprostinil diethanolamine.

20. The method of claim 18, wherein the administering results in a minimum plasma concentration of treprostinil in the subject from 0.1 ng/ml to 0.2 ng/ml.

21. The method of claim 18, wherein the administering results in a maximum plasma concentration of treprostinil in the subject from 0.5 ng/ml to 2 ng/ml.

22. The method of claim 18, wherein said administering is performed twice a day or once a day.

23. The method of claim 18, wherein said administering is performed twice a day.

* * * * *